United States Patent [19]
Zamir et al.

[11] Patent Number: 5,965,752
[45] Date of Patent: Oct. 12, 1999

[54] PREPARATIVE SCALE ISOLATION AND PURIFICATION OF TAXANES

[75] Inventors: Lolita Zamir, Westmount; Gaetan Caron, Laval des Rapides, both of Canada

[73] Assignee: Institut National De La Recherche Scientifique, Sainte-Foy, Canada

[21] Appl. No.: 08/919,066

[22] Filed: Aug. 22, 1997

Related U.S. Application Data

[60] Provisional application No. 60/024,503, Aug. 23, 1996.

[51] Int. Cl.$^6$ .................................................. C07C 305/14
[52] U.S. Cl. ............................................. 549/510; 560/107
[58] Field of Search ............................ 549/510; 560/107; 424/195.1

[56] References Cited

U.S. PATENT DOCUMENTS

| | | | |
|---|---|---|---|
| 5,380,916 | 1/1995 | Rao | 560/170 |
| 5,407,674 | 4/1995 | Gabetta et al. | 514/449 |
| 5,480,639 | 1/1996 | ElSohly et al. | 514/449 |

OTHER PUBLICATIONS

MacGuire et al., (1989), *Annals. of Internal Medicine*, vol. 111, p. 273.
Rowinsky et al., (1990), *Journal of the National Cancer Institute*, vol. 82: 1247–1259.
Huang et al., (1986), *J. Natl. Prod.*, vol. 49, p. 665.
Miller et al., (1981), *J. Org. Chem.*, vol. 46, p. 1461.
McLaughlin et al., (1981), *J. Nat. Rod.*, vol. 44, p. 312.
Kingston et al., (1982), *J. Nat. Prod.*, vol. 45, p. 466.
Senilh et al., (1994), *J. Natl. Prod.*, vol. 47, p. 131.
Zamir et al., (1992), *Tetrahedron Letters*, vol. 33, p. 5173.

*Primary Examiner*—Amelia Owens
*Attorney, Agent, or Firm*—McDonnell, Boehnen, Hulbert & Berghoff

[57] ABSTRACT

This invention relates to an improved method for isolating taxanes by using a preparative scale technique amenable to commercial production. This method provides high yields of known taxanes in addition to new taxanes.

14 Claims, 1 Drawing Sheet

PREPARATIVE SCALE ISOLATION AND PURIFICATION OF TAXANES

This application claims benefit of provisional application Ser. No. 60/024,503 filed Aug. 23, 1996.

FIELD OF THE INVENTION

This invention relates to the isolation and purification of taxanes from naturally occurring, Taxus species, and more particularly, to an improved method for isolating taxanes by using a preparative scale technique amenable to commercial production.

BACKGROUND OF THE INVENTION

For hundreds of years most drugs were highly impure mixtures of composition derived primarily from plant or animal origin. As recently as the 1920's most active ingredients were used in only partially purified forms. Since then, vastly improved tools and methods for the purification of chemical compounds have been developed enabling identification of compounds that produce beneficial effects. This field science has become known generally as Natural Products Chemistry.

The foundation of Natural Products Chemistry rests on extraction, isolation and purification strategies. As is well appreciated in the art, different isolation procedures oftentimes yield a different profile of chemical compounds. Seemingly minor changes to an isolation procedure such as changing a solvent, the ratio of solvent or even the type of filter paper can result in large changes in the type, amount and purity of chemical compounds obtained. One procure designed to yield large quantities of a crystalline compound, might inadvertently eliminate or inactivate an even more valuable compound in the first extraction step.

A family of compounds isolated from the very slow growing yew (genus Taxus, family Taxaceae), have gained notoriety since the discovery that Taxol was found to be an effective cancer chemotherapeutic agent and was approved by the FDA for treatment of ovarian carcinoma. Since the recognition of Taxol's anticancer activities, research efforts to isolate other compounds from trees of the Genus Taxus have intensified to find improved methods of purification, and synthetic procedures.

Today, the taxane family of terpenes are considered as an exceptionally promising group of cancer chemotherapeutic agents. At least 60 different compounds have been reported in the literature posessing a taxane nucleus (4,8,12,15,15-pentamethyltricyclo[$9.3.1.0^{3,8}$] pentadecane).

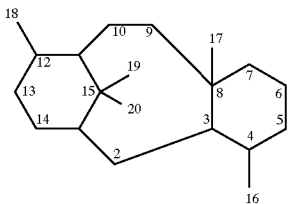

Many taxane derivatives, including taxol, taxotere, and cephalomannine are highly cytotoxic and have been shown to be effective against leukemia, advanced breast and ovarian cancers in clinical trials (W. P. MacGuire et al., *Annals of Internal Medicine*, vol 111, pg. 273, 1989). They have also exhibited promising activity against a number of other tumor types in preliminary investigations. Taxanes are believed to exert their antiproliferative effect on taxane sensitive cells by inducing tubulin polymerization, thereby forming extremely stable and nonfunctional microtubules (Eric K. Roxinsky et al., Journal of the National Cancer Institute, Vol. 82:1247–1259, 1990).

A major problem with all of the clinical studies is the limited availability of taxanes. For example, the only available natural source for taxol to date are several species of a slow growing Yew (genus Taxus), wherein Taxol is only found in very low concentrations (less than 400 parts per million) in the bark of these trees. Furthermore the extraction is difficult, the process is expensive and the yield of taxol is low (Huang et al., J. Nat. Prod. 49 665 1986 reported a yield of 0.01% taxol from *Taxus brevifolia* bark).

The number of patents describing the isolation and purification of taxol and taxanes from Taxus bark is increasing.

The procedures currently known for isolating taxol are very difficult and low-yielding. For example, a yield of 0.01% was reported from a large scale isolation starting with at least 806 lbs of *Taxus brevifolio* bark (Huang et al., J. Nat. Prod., 49:665, 1986). The isolation of taxol was described by other workers: Miller et al., J Org. Chem., 46:1469, 1981; McLaughlin et al., J. Nat. Prod., 44:312, 1981; Kingston et al., J. Nat. Prod., 45:466, 1982, and Senih et al., J. Nat. Prod., 47:131, 1994, U.S. Pat. No. 5,407,674 and U.S. Pat. No. 5,380,916. The reported yields of taxol from various species of yew range from 50 mg/kg to 165 mg/kg (i.e., 0.005–0.017%).

Koppaka (U.S. Pat. No. 5,380,916) describes a method for isolating taxol and its analogues from a crude extract of *Taxus brevifolia* and *Taxus floridana*, charactized by treating the crude extract by reverse phase liquid chromatography on an adsorbant, and recovering a number of compounds in pure form by elution. However, reverse phase chromatographic separation of impure taxanes from plant materials is expensive because of the cost of the column materials. Generally reverse phase separation can be used on the crude extraction from bark of some of the Taxus species because of the relatively low concentration of pigments, lipids and waxes and high concentration of taxol; however, the needles tend to contain lesser amounts of taxol and significant amounts of impurities and thus reverse phase chromatography for separation of taxanes form early stages of purification is not practical.

EsSohly et al. (see U.S. Pat. No. 5,480,639), describe methods of obtaining taxanes, comprising extracting and purifying a number of taxanes from ornamental cultivars using a series of organic and aqueous solvents and normal phase chromatography.

Methods of synthesis for the taxane ring skeleton are difficult, producing compounds deficient in pharmacological activity and are currently more expensive than isolation from the plant material. Thus, despite low yields, it is likely that the Taxus plant will remain a predominant reliable supply source for clinical quantities of taxol and its related compounds for years to come.

Although the use of taxol is successful against a number of specific tumor types, it is not universally effective. Hence, there is an urgent need for novel compounds from the taxane family which are closely related to taxol in their chemical structures but with more potent chemotherapeutic activities. New isolation procedures will lead to the purification and identification of new compounds. Moreover, a need exists to simplify the current procedures to produce taxanes and reduce the cost of such production by using simplified extraction and chromatographic techniques.

Therefore, purification techniques which provide high yields of known taxanes and new taxanes are needed to provide greater quantities of these promising therapeutic agents. The present invention provides a purification technique which accomplishes these goals.

SUMMARY OF THE INVENTION

Due to the immediate requirement for high yields of known taxanes and additional novel taxanes, the current invention is concerned with the isolation and purification of taxanes.

Accordingly, it is an object of this invention to provide a consistent method directed towards isolating compounds from plant matter derived from the Taxus genus of plants.

It is a further object of this invention to provide a method for the isolation of taxanes from plant matter that is easier than existing methods.

It is also an object of this invention to provide a method for the isolation of taxanes from plant matter that is on a preparative scale.

It is a further object of this invention to provide a method for the isolation of taxanes that uses less chromatographic columns, and in particular, less HPLC than existing methods.

These and other objectives, as well as the nature, scope and utilization of this invention, will become readily apparent to those skilled in the art from following the description, the drawings and the appended claims.

DETAILED DESCRIPTION OF INVENTION

Figure 1:
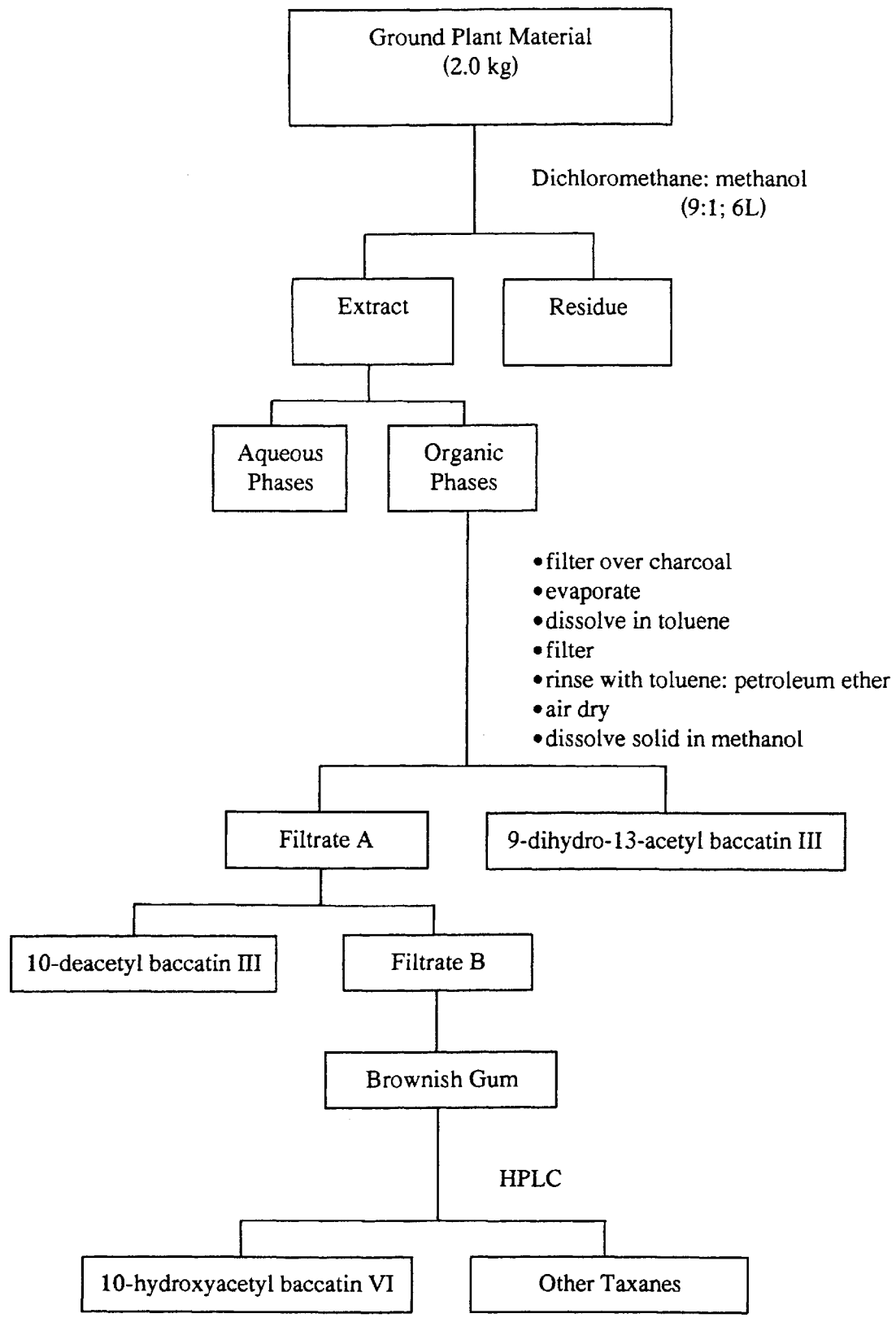
FIG. 1 shows a separation scheme for isolating taxanes from *Taxus canadensis* in accordance with this invention.

The starting material for use in this invention is vegetal material, selected from a group of plants commonly referred to as taxads. The most suitable plants of this group are the species Taxus. Amongst the Taxus species, *Taxus canadensis* A the preferred source for use in the isolation and purification of the novel taxane claimed in this invention. *Taxus canadensis* is a small ramping bush abundant in Quebec, Canada which seems to differ from other yews in the content of its taxanes. 9-dihydro-13-acetylbaccatin III is found in concentrations 3–7 times greater than taxol (Zamir L. O. et al. Tetahedron Letters 33 5173 1992).

The method disclosed is effective when using the roots or bark of the Taxus bushes but, as previously discussed, we consider it prudent to use a source that is rapidly regenerated (such as the leaves i.e. needles) and therefore in abundant supply.

The present invention describes a method for the isolation of taxanes from *Taxus canadensis*. This method was used successfully for the isolation of taxanes present in the plant material.

One particular advantage of this technique is that 10-deacetyl-baccatin III and 9-dihydro-13-acetylbaccatin III (an abundant taxane specific to *T. canadensis* needles) can be isolated by simple recrystallisations and preparative reverse phase HPLC instead of many silica gel columns.

The present invention will now be illustrated, but is not limited to be limited, by the following examples.

EXAMPLE 1

Isolation of Taxanes from *Taxus canadensis*

The plant material was collected in Quebec. The needles were stored at 4° C. in sterilized sand and peat moss and were dried before grinding. The needles were extracted by adding methanol (0.6 L) and dichloromethane (5.4 L) to a 20 L glass container equipped with a mechanical stirrer. Stirring is adjusted to 1.0–1.5 rotations per second and the dried/ ground needles of *Taxus canadensis* (1.5 kg) are added gradually over a period of 30 minutes. The mixture is stirred for one hour and another 0.5 kg of needles (total of 2.0 kg) is added over a period of 10 minutes. After stirring for 24 hours the mixture is filtered over a Whatman paper #1 using a buchner funnel and an erlenmeyer flask with a slight vacuum. The needles are returned to the glass container and 3.0 L of dichloromethane:methanol (9:1) are added. The mixture is stirred for 24 hours and filtered. This time the needles are washed with 1.0 L of dichloromethane:methanol (9:1). This second filtrate is added to the first.

Washing the Extract with Water: Water (0.5 L) is added to the combined filtrate and stirred vigorously for 15 minutes or later which time the aqueous phase is removed from the mixture. This washing procedure is repeated three more times. The organic phase is not immediately evaporated but is filtered directly over charcoal.

Filtration of the Extract over Charcoal: The charcoal filter is prepared as follows: Norit SA3 charcoal (0.5 kg: 100 mesh—Aldrich) is mixed with celite(0.5 kg: AC 2098T-Anachemia) and placed into a course scintered glass funnel. The charcoal-celite mixture is soaked with dichloromethane:methanol (9:1) and washed with an additional 1.0 L of that solvent. The extract is filtered on this bed of charcoal which is then washed with 1.5 L of dichloromethane:methanol (9:1). The mixture is evaporated under vacuum using a rotovap and the residue is left under high vacuum for one hour using a vacuum pump to remove all traces of methanol.

Precipitation: The residue is dissolved in 0.2 L of toluene and transferred to a 2.0 L erlenmeyer flask. The solution is magnetically stirred while petroleum ether 35"–60° (0.2 L) is added dropwise over a period of 25 minutes. To avoid the formation of large lumps of solid, it is essential to have a fast uninterrupted stirring during addition. At the end of this addition, the mixture is stirred for an additional 15 minutes and filtered in the usual manner (buchner funnel with Whatman paper). The solid is not left to dry but is rinsed with 70 mL of toluene:petroleum ether (1:1). The solid is then air dried for 15 minutes.

Isolation of A Major Taxane, 9-dihydro-13-acetylbaccatin III: The solid is transferred to a 200 mL erlenmeyer flask and dissolved in 100 mL of methanol. After one hour, crystals of 9-dihydro-13-acetlybaccatin III are observed and the mixture is left at −20° C. for 18 hours to favor crystallization. The solid is filtered in the usual manner and washed with 2×10 mL, of cold methanol. The filtrate and the washings are kept aside for the next step (Filtrate A). The solid is often contaminated with black particles of charcoal which probably passes through the scintered glass during the charcoal filtration. To eliminate these particles, dichloromethane (20 mL) is added to the solid which dissolves rapidly and the insoluble black particles are filtered. The filtrate is evaporated on a rotovap, dichloromethane (2.0 mL) is added to dissolve the residue followed by methanol (80 mL) to induce crystallization. The mixture is left at −20° C. for 18 hours and filtered. The filtrate and washings are combined with Filtrate A. The solid is washed with cold methanol (5×1 mL) and dried under vacuum for 2 hours affording 1.2 g of 9-dihydro-13-acetyl baccatin III as a white product.

Isolation of 10-deacetylbaccatin III: Filtrate A is evaporated on a rotovap and acetonitrile (25 mL) is added.

10-deacetylbaccatin III is left to crystallize at room temperature for 18 hours, filtered and washed with 10 mL of acetonitrile. The filtrate and washings are kept aside for the next step (Filtrate B). A mixture of dichloromethane:methanol (1:1, 2 mL) is added to the solid which dissolves completely and acetonitrile (80 mL) is added to induce crystallization. After 18 hours at room temperature, the solid is filtered and washed with 10 mL of acetonitrile. The filtrate and washings are combined with Filtrate B. The solid is dried under vacuum for two hours affording 0.2 g of 10-deacetylbaccatin III as a brownish, slightly impure solid.

Removal of Water Soluble and Petroleum-Ether Soluble Components: Filtrate B is evaporated and the residue (15.0 g) is dissolved in actonitrile:methanol (1:1, 12 mL) The solution is stirred while petroleum-ether (100 mL) is added over a period of 10 minutes followed by water (10 mL) over 5 minutes. More water (140 mL) is added more rapidly over 10 minutes with stirring. The mixture involving two liquid phases and an insoluble residue is left standing for 0.5 hour with occasional shaking. During that time the insoluble gum hardens. The liquid phases are decanted; water is added over the gum and decanted. Drying under vacuum afforded 12.4 grams of a brownish gum which contains taxol as the major component along with a series of minor taxanes and other products as shown by HPLC analysis.

Isolation of Taxanes with Reverse Phase HPLC: Taxanes in the brown solid are separated on a preparative HPLC using an ODS-2 reverse phase column (2.0×50 cm; Whatman) and a Waters Delta Prep 3000 instrument coupled to a model 481 variable wavelength detector at 227 nm. The products are eluted with a gradient over 140 minutes of acetonitrile:water (25:75) to 100% acetonitrile. At 55.5 min, a peak comprising 10 hydroxyacetylbaccatin VI, among other taxanes is collected.

Purification of Taxanes Through Silvated Derivatives: The collected fraction is evaporated and dissolved in dry DMF (1.0 mL). Imidazole (60 mg) is added followed by triethylsilylchloride (100 mL). The solution is stirred at room temperature for 24 hours and water (3 mL) is added followed by ethyl acetate (3.0 mL). The phases are separated and the aqueous phase is extracted with ethyl acetate (2×3 mL). The combined organic extracts are washed with water (3×3 mL) and dried over magnesium sulphate. The mixture is filtered and evaporated. The residue is chromatographed on the same preparative HPLC system eluting with a gradient over 50 minutes of acetonitrile:water (70:30) to 100% acetonitrile. Peaks are collected which consists Taxanes as their silyl derivatives. The solvent is evaporated and a solution of HCl 0.10 N in 95% ethanol is added (2.0 mL). After the solution was left standing for 48 hours it is evaporated and chromatographed on the preparative HPLC system, eluting with a gradient over 50 minutes of acetonitrile:water (25:75) to 100% acetonitrile.

Final Purification on Analytical HPLC: is performed using the analytical HPLC described above and eluting with water:acetonitrile (29:21).

It is to be understood that the examples described above are not meant to limit the scope of the present invention. It is expected that numerous variants will be obvious to the person skilled in the art to which the present invention pertains, without any departure from the spirit of the present invention. The appended claims, properly construed, form the only limitation upon the scope of the present invention.

We claim:

1. A process for the purification of taxanes from plant material of a taxus genus which comprises the following steps:

(i) extracting organic matter from a Taxus genus into an organic solvent to form an extract;

(ii) washing said extract with one or more aqueous phases to yield a washed organic extract;

(iii) contacting said washed organic extract with charcoal;

(iv) substantially removing solvent from said organic extract to form a residue;

(v) substantially taking up said residue in a volume of a first organic solvent to form a solution and whilst agitating the solution gradually adding a second organic solvent, wherein said second solvent is of lower polarity than said first solvent, precipitating a solid;

(vi) recrystallizing said precipitated solid to form a crystalline product; and (vii) separating said crystalline product from its mother liquor.

2. A process for the purification of taxanes from an extract of plant material of a taxus genus which comprises the following steps:

(i) substantially taking up the extract of plant material of a taxus genus in a volume of a first organic solvent to form a solution and whilst agitating the solution gradually adding a second organic solvent, wherein said second solvent is of lower polarity than said first solvent, precipitating a solid;

(ii) recrystallizing said precipitated solid to form a crystalline product; and (iii) separating said crystalline product from its mother liquor.

3. A process for the purification of taxanes from plant material according to claim 1 or 2 which additionally comprises the step of recystallizing said crystalline product.

4. A process for the purification of taxanes from plant material according to claim 1 or 2, which additionally comprises the steps of substantially removing solvent from said mother liquor to form a residue and recrystallizing said residue from a polar solvent to yield a taxane and a second mother liquor.

5. A process for the purification of taxanes from plant material according to claim 4, which additionally comprises the steps of substantially removing solvent from said second mother liquor to form a residue and washing the residue with water and hydrocarbon solvent to yield a gum containing taxol.

6. A process for the purification of taxanes from plant material according to claim 5, which additionally comprises subjecting said gum to reverse phase HPLC to obtain a faction containing a taxane.

7. A process for the purification of taxanes from plant material according to claim 6, which additionally comprises the step of subjecting a hydroxy group of a taxane in said fraction to a silyating reagent to form a silyl derivative of said taxane and subjecting said silyl derivative of said taxane to preparative HPLC to purify said taxane silyl derivative.

8. A process for the purification of taxanes from plant material according to claim 7, which additionally comprises the step of hydrolysing said silyl derivative of said taxane to regenerate a taxane and further subjecting said taxane to preparative HPLC.

9. A process for the purification of taxanes from plant material according to claim 1 or 2, wherein said first solvent is selected from the group consisting of an alkyl-aromatic, a $C_1$–$C_8$-alkyl alcohol, a $R_1R_2C=O$, wherein $R_1$ or $R_2=C_1$–$C_8$-alkyl, an ether, a dioxane, tetahydrofuran, DMSO, DMF, an ester, halocarbons, perfluorocarbon, and haloaromatics, and said second solvent is selected from the group consisting of linear hydrocarbons, branched hydrocarbons, cyclic-hydrocarbons and halocarbons.

10. A process for the purification of taxanes from plant material according to claim 9, wherein said first solvent is selected from the group consisting of toluene, ethylbenzene, o-xylene, m-xylene, p-xylene, diethylether, acetone, ethylacetate, chlorobenzene, dichloromethane, and cloroform and said second solvent is selected from the group consisting of cyclohexane, cyclopentane, n-hexane, n-pentane, n-heptane, petroleum ether, and carbontetrachloride.

11. A process for the purification of taxanes from plant material according to claim 9, wherein said first solvent is toluene and said second solvent is petroleum ether.

12. A process for obtaining taxanes from *Taxus canadensis* which comprises
   (a) drying the vegetal material obtained from the Taxus plant at a temperature of between 20° C. and 70° C. to form dried plant matter;
   (b) contacting the dried plant matter from step (a) with an organic solvent that is, or an equivalent organic solvent whose polarity is equivalent to, a solution of methanol:dichloromethane ranging in concentration from 1:5 to 1:15 so as to extract a crude taxane mixture in the extracting solvent mixture;
   (c) washing the extract of (b) with water;
   (d) filtering the extract over charcoal;
   (e) evaporating the filtered extract of (d) to remove organic solvent leaving a residue;
   (f) dissolving the residue of (e) in toluene, or an equivalent organic solvent, to which petroleum ether, or an equivalent organic solvent, is added under fast uninterrupted stir to form a residue-solution;
   (g) filtering the residue-solution of (f) to accumulate a solid;
   (h) drying the solid of (g); and
   (i) dissolving the dried solid of (h) in methanol or an equivalent organic solvent to crystallize 9-dihydro-13-acetylbaccatin III out of said dissolved dried solid and filtering to separate into a solid and a filtrate A.

13. The process according to claim 12, which additionally comprises:
   (a) substantially evaporating the filtrate A of step (i) and dissolving the residue thereby generated in acetonitrile or an equivalent solvent;
   (b) crystallizing 10-deacetylbaccatin III out of said the solution of step 2(a) and filtering to separate into a solid and a filtrate B.

14. The process according to claim 13, which additionally comprises:
   (a) substantially evaporating the filtrate B of step (b) and dissolving the residue thereby generated in a solution of acetonitrile:methanol or a solvent of equivalent polarity to generate an organic solution;
   (b) adding petroleum-ether or equivalent solvent to the organic solution of step 14(a) under stirring to generate a mixed organic solution;
   (c) adding water to the mixed organic solution of step 14(b) to generate a biphasic solution to generate an insoluble gum within a liquid phase;
   (d) decanting the liquid phase of step 14(c) to separate the insoluble gum from the liquid phase;
   (e) drying the insoluble gum of step 14(d) to generate a brown solid;
   (f) chromatographically separating the taxanes in the chromatograhic solvent mixture on a normal phase chromatographic column containing silica gel as an absorbent for the crude taxane at a pressure which provides the separation between about 1 mm of mercury and 100 psi, using an acetonitrile:water (25:75) to 100% acetonitrile, or equivalent solvent gradient
   (g) collecting a fraction comprising 10 hydroxyacetylbaccatin VI among other taxanes;
   (h) generating the silyl derivatives of the taxanes contained within the fraction of step 14(g);
   (i) chromatographically separating the silyl derivatives of the taxanes on a normal phase chromatographic column containing silica gel as an absorbent for the crude taxane at a pressure which provides the separation between about 1 mm of mercury and 100 psi, using an acetonitile:water (25:75) to 100% acetonitrile, or equivalent solvent gradient; and
   (j) removing the silyl groups from the taxanes.

\* \* \* \* \*